(12) United States Patent
Schmidt et al.

(10) Patent No.: US 7,364,912 B2
(45) Date of Patent: Apr. 29, 2008

(54) CONTROLLING THE FLOW OF HYDROGEN AND AMMONIA FROM A HYDROGEN GENERATOR DURING A BREAKTHROUGH WITH HYDRATED COPPER (II) CHLORIDE TRAP

(76) Inventors: Jeffrey A. Schmidt, 1192 E. Riverbend St., Superior, CO (US) 80027; Franklin Earl Lynch, 10458 Christopher Dr., Conifer, CO (US) 80433; John S. Wilkes, 2845 Palmer Divide Rd., Larkspur, CO (US) 80118

(*) Notice: Subject to any disclaimer, the term of this patent is extended or adjusted under 35 U.S.C. 154(b) by 447 days.

(21) Appl. No.: 10/259,220

(22) Filed: Sep. 26, 2002

(65) Prior Publication Data
US 2003/0068264 A1    Apr. 10, 2003

Related U.S. Application Data

(60) Provisional application No. 60/327,639, filed on Oct. 5, 2001.

(51) Int. Cl.
*G01N 33/00* (2006.01)
(52) U.S. Cl. ............... 436/144; 436/113; 436/148; 436/55
(58) Field of Classification Search ........... 436/144, 436/55, 113, 148, 164
See application file for complete search history.

(56) References Cited

U.S. PATENT DOCUMENTS 5,037,624 A * 8/1991 Tom et al. ............... 423/210

(Continued)

FOREIGN PATENT DOCUMENTS

JP    10244149 A  * 9/1998

OTHER PUBLICATIONS

Ivanova et al. "Effect of moisture on the adsorption of ammonia by chemisorbents based on fibrous activated carbons" Kolloidnyi Zhurnal (1984), 46(4), 778-82, Abstract.*

(Continued)

*Primary Examiner*—Yelena G. Gakh
(74) *Attorney, Agent, or Firm*—AFMCLO/JAZ; Fredric L. Sinder (57) ABSTRACT

Gas flow is controlled to a feed gas consuming device depending on whether a contaminant gas is present. In one embodiment, hydrogen gas flow from a hydrogen gas generator to a hydrogen consuming device, such as a fuel cell, gas chromatograph or a flame ionization detector, is terminated when there is chemical contaminant breakthrough in the hydrogen gas flow. The apparatus relates to the use of a sensor for detecting a predetermined concentration of a chemical contaminant such as ammonia. In one embodiment the apparatus terminates the gas flow when a concentration of ammonia in the gas flow corresponds to a breakthrough (e.g., approximately in the range of 2.0% or greater). The apparatus prevents the ammonia-contaminated hydrogen from disabling such a hydrogen consuming device that would have otherwise received the contaminated gas flow. The apparatus terminates such a hydrogen contaminated gas flow by exposing a breakthrough detection material to the gas flow, wherein this material is substantially only reactive to concentrations of a predetermined contaminant (e.g., ammonia) for terminating the gas flow when such concentrations are indicative of a breakthrough of the contaminant. For instance, such a material may undergo a readily discernible change when in the presence of at least a predetermined concentration of the contaminant corresponding to a breakthrough. Such a discernible change in the breakthrough detection material may be, e.g., one or more of: a change in volume, density, opacity, color and/or electrical conductivity or potential. The detection material may be used in series with other substances that chemically and physically capture impurities in the gas flow until the detection material reacts, stopping the flow of hydrogen to the hydrogen consuming device.

4 Claims, 6 Drawing Sheets

U.S. PATENT DOCUMENTS

| | | | | |
|---|---|---|---|---|
| 5,669,961 | A * | 9/1997 | Baker et al. | 95/115 |
| 6,168,645 | B1 * | 1/2001 | Succi et al. | 95/8 |
| 6,274,093 | B1 | 8/2001 | Long et al. | 422/129 |
| 2002/0028171 | A1 * | 3/2002 | Goetsch et al. | 423/237 |
| 2003/0035087 | A1 * | 2/2003 | Murayama | 355/30 |

OTHER PUBLICATIONS

Uribe et al. "Effect of ammonia as potential fuel umpurity on proton exchange membrane fuel cell performance", J. Electrochm. Soc., 2002, v. 149, No. 3, pp. A293-A296.*

* cited by examiner

Fig. 9

CONTROLLING THE FLOW OF HYDROGEN AND AMMONIA FROM A HYDROGEN GENERATOR DURING A BREAKTHROUGH WITH HYDRATED COPPER (II) CHLORIDE TRAP

The present application claims priority from and the benefit of U.S. Provisional Patent Application No. 60/327,639 filed Oct. 5, 2001, which is fully incorporated herein by reference.

FIELD OF THE INVENTION

The present invention is related to regulating gas flow when a trace contaminant is present. In particular, the present invention relates to preventing a contaminated hydrogen gas flow, which may include ammonia, from reaching a hydrogen consuming device such as a fuel cell.

BACKGROUND INFORMATION

Hydrogen gas generators are known wherein hydrogen gas is generated by, e.g., a reaction between ammonia ($NH_3$) and a solid reactant such as lithium aluminum tetrahydride. The resulting hydrogen gas is generally contaminated with ammonia which must be filtered from generated hydrogen gas stream prior to this stream entering a device (e.g., a fuel cell, a gas chromatograph, or a flame ionization detector) that uses hydrogen. Only trace amounts of ammonia are contained in the generated gas mixture up until the generator is substantially depleted of its ability to generate hydrogen gas. Such trace amounts of ammonia can be filtered from the generated gas by providing a material or substance (denoted a "getter" or "getter material" herein) that extracts the ammonia from the generated gas. Prior techniques for performing such filtering of chemical contaminants such as ammonia from contacting the anode of a fuel cell have included direct particle filtration combined with a consumable getter material as shown in U.S. Pat. No. 6,274,093, filed Aug. 6, 1998 and incorporated fully by reference herein. Successful getter materials for the removal of ammonia have included an adsorption material such as zeolite, activated charcoal and/or sodium hydrogen sulfate monohydrate ($NaHSO_4.H_2O$). Note that $NaHSO_4.H_2O$ reacts chemically with and permanently traps $NH_3$ from the $H_2$ stream.

However, when the hydrogen generating reaction within the generator approaches the end of the reaction's ability to generate hydrogen, the concentration of ammonia (or other contaminant) in the generated gas can increase abruptly and substantially. Such an increase in a contaminant (e.g., ammonia) concentration is denoted herein as a "breakthrough." Moreover, such a breakthrough will eventually overcome the ability of the getter material to filter the contaminant from the gas stream since the getter becomes spent or saturated from reactions with the contaminant in the $H_2$ stream. Accordingly, the contaminant in the gas stream will accumulate and, at least in the case of ammonia, disable the device receiving the hydrogen gas stream unless the high concentrations of ammonia are prevented from entering the device.

Accordingly, it would be desirable to have a method and apparatus that would inhibit passage of the $NH_3$ contaminated hydrogen into the hydrogen consuming device by stopping the $H_2$ and $NH_3$ gas mixture flow once there is ammonia breakthrough into the generated gas stream. It would also be desirable provide getter materials with large capacities for trapping $NH_3$ for thereby extending the effective operating time and total hydrogen delivered from a hydrogen gas generator. Moreover, it would be desirable for such a method and apparatus to detect changes in the gas stream $NH_3$ concentration, and/or rate of concentration change in simple, reliable, and cost effective manner. Additionally, in at least some contexts it would be desirable for the method and apparatus to be substantially passive in the sense that a chemical reaction between the breakthrough ammonia and a breakthrough detection material can, e.g., plug the line providing the generated gas stream so that the gas stream ceases to flow into the device. It would also be advantageous to prevent passage of any unwanted gas to a feed gas consuming device that might not consume hydrogen.

SUMMARY OF THE INVENTION

The present invention is directed to controlling gas flow when a feed gas and a contaminant gas are present. In a preferred embodiment, hydrogen gas flow from a hydrogen gas generator to a device (such device being e.g., a fuel cell, a gas chromatograph, a flame ionization detector, or other hydrogen utilizing device) is prevented when there is chemical contaminant breakthrough in the hydrogen gas flow. Thus, the present invention may be considered a sensor for detecting a predetermined concentration of a chemical contaminant such as ammonia. In particular, the present invention terminates the gas flow when the concentration of ammonia in the gas flow corresponds to a breakthrough (e.g., approximately in the range of 2.0% or greater by volume). Thus, the present invention prevents the ammonia contaminated hydrogen from disabling a device that would have otherwise received the contaminated gas flow. Moreover, the present invention terminates such a hydrogen contaminated gas flow by exposing a material to the gas flow, wherein this material is substantially only reactive to concentrations of a predetermined contaminant in the gas flow when such concentrations are indicative of a breakthrough of the contaminant. For instance, such a material (denoted herein a "breakthrough detection material") may undergo a readily discernible change when in the presence of at least a predetermined concentration of the contaminant corresponding to a breakthrough. Such a discernible change in the breakthrough detection material may be, e.g., one or more of: a change in volume, density, opacity, color and/or electrical conductivity or potential.

In one embodiment, the breakthrough detection material for detecting breakthrough concentrations of ammonia may be any one of a number of anhydrous metal salts, and/or hydrated multivalent transition metal halide, sulfate, and/or nitrate complexes. Such hydrated complexes can exchange water ligands for the ammine ligands thereby producing metal ammine complexes. In particular, such a breakthrough detection material may include one or more of:

(1) anhydrous $CuCl_2$,
(2) hydrated and anhydrous $CoCl_2$, and $AlCl_3$
(3) hydrated cobalt (II and III) chloride and sulfate,
(4) hydrated copper (II) chloride and sulfate,
(5) hydrated chromium (II and III)) chloride and sulfate, and
(6) hydrated nickel (II) chloride and sulfate.

More particularly, hydrated copper (II) chloride ($CuCl_2.2H_2O$) has been found to be especially labile and reacts rapidly with ammonia at breakthrough concentrations.

Various embodiments of the present invention are contemplated depending, e.g., on the environment and the application in which the present invention is to be used. In one embodiment, the breakthrough detection material is provided in a component or assembly that is designed to be replaceable separately from one or both of the hydrogen generator and device being supplied with hydrogen gas from the generator. Moreover, this separate component may also include a getter material for the removal of the non-breakthrough traces of the contaminant in the hydrogen gas, wherein such a getter material (e.g., zeolite, $NaHSO_4.H_2O$, and/or a getter mixture including $CuCl_2.2H_2O$) when the contaminant is ammonia) may be upstream of the breakthrough material thereby further assuring that the breakthrough material does not prematurely react with the contaminant in the hydrogen gas stream. Additionally, this separate component may also include such a getter material downstream of the breakthrough detection material and/or an additional contaminant adsorption material such as activated charcoal for filtering any contaminant(s) in the gas flow that bypass the breakthrough detection material and any initial upstream getter material prior to the termination of the gas flow to the device. Thus, this separate component may be considered a type of fuse for both preventing ammonia contaminated hydrogen from entering an attached hydrogen consuming device and for indicating when the attached upstream hydrogen generator has substantially depleted its capacity for generating hydrogen. However, other embodiments may incorporate various of the breakthrough detection materials, the upstream or downstream getter materials, and/or additional contaminant absorbers into the hydrogen generator and/or a device.

In one embodiment of the present invention, the breakthrough detection material may be provided in a hydrogen gas conduit between the hydrogen generator and a device in a manner so that the breakthrough detection material is porous enough so that hydrogen with possibly trace amounts of one or more contaminants (e.g., ammonia) flow therethrough without plugging the conduit. However, the breakthrough detection material is packed sufficiently densely within the conduit so that shortly after contact with a breakthrough concentration of the contaminant, the breakthrough detection material forms a plug in the conduit that halts the flow of the gas stream to the device. Note that the typical packing density is generally greater than 50% of the theoretical crystalline density for the solid form of the breakthrough detection material (e.g., hydrated copper (II) chloride ($CuCl_2.2H_2O$)). Moreover, in one experiment, it was determined that $CuCl_2 2H_2O$ had a five- to tenfold expansion upon reaction with ammonia. This implies a similar change in packing density when confined as disclosed here.

In another embodiment, upon reacting with the contaminant, a change in the size of the breakthrough detection material triggers the release of, e.g., a spring loaded valve for terminating the gas flow to a device. In particular, when the breakthrough detection material includes, e.g., $CuCl_2 2H_2O$ and the contaminant is ammonia, the $CuCl_2 2H_2O$ expands when reacting with the ammonia and such expansion can be used to release the spring-loaded valve so that it shuts off the gas flow.

In another embodiment, a change in, e.g., the color of the breakthrough detection material when reacting with a contaminant in the hydrogen gas stream may be optically detected and a gas flow shut off device may be, e.g., electronically or mechanically activated to terminate gas flow to a device.

Optionally in some embodiments, there may be visual or other indicators provided that allow a user to determine the state or extent to which a hydrogen generator has depleted its ability to produce hydrogen. In particular, such indicators may provide the user with an indication, prior to and/or after breakthrough of a contaminant, as to the characteristics of the gas mixture that has been recently generated as well as the extent to which the hydrogen generator has been depleted and/or is likely to continue to generate hydrogen gas. For example, by providing a breakthrough material such as $CuCl_2.2H_2O$, and a window along the gas stream flow to allow the user to view the changes in the breakthrough material, the user may be able to gauge the state of the hydrogen generator and the gas mixture being produced therefrom since light blue-green $CuCl_2.2H_2O$ turns dark blue when it comes in contact with a concentration of ammonia of, e.g., approximately 2.0% or greater. However, alternative indicators may also be provided by other embodiments of the invention. For instance, by providing a getter material (and/or composite with another material) that, e.g., changes color as it absorbs the contaminant, and by also providing a window along the gas stream flow, the user may be able to gauge the state of the hydrogen generator. Alternatively, by interleaving, across the gas stream flow, layers of a getter material with a second material that changes color upon contact with a predetermined amount and/or concentration of the contaminant, the user may also be able to gauge the state of the hydrogen generator via an adjacent window along the gas stream flow. Note that the second material may include one of the substances identified in (i) through (v) above. Moreover, note that calibration information (e.g., indicia and/or color indications) may also be provided by embodiments of the invention so that the user can visibly compare the characteristics of the materials in the gas flow with such calibration information for thereby more reliably determining the characteristics of the gas flow and/or the state of the hydrogen generator.

Additional features and benefits of the present invention will become evident from the accompanying drawing and Detailed Description herein below.

DETAILED DESCRIPTION

Figure 1:
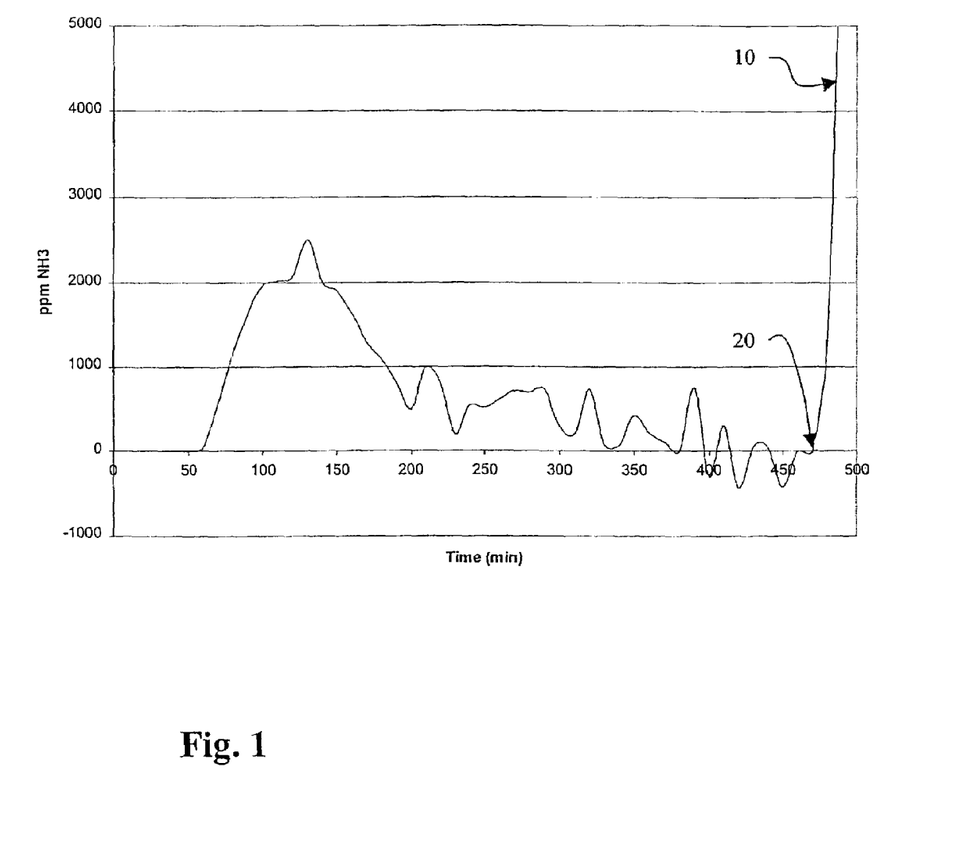
FIG. 1 shows a graph of the concentration of ammonia in the hydrogen gas stream, over time, for such a hydrogen generator.

In operation, hydrogen produced by a hydrogen generator (reactor) such as is disclosed in U.S. Pat. No. 6,274,093, filed Aug. 6, 1998 (and incorporated fully by reference herein) is contaminated by traces of $NH_3$ in a range of approximately 0 to 2,500 parts per million (ppm) while the generator has not substantially depleted its ability to generate hydrogen. FIG. 1 shows a graph of the concentration of ammonia in the hydrogen gas stream, over time, for such a hydrogen generator. The graph 10 of FIG. 1 is an approximation of the concentration of ammonia in parts per million (as indicated by the right Y-axis) over time. Note that the negative ammonia concentrations at times around 400 minutes are due to the small concentration of the ammonia in the generated hydrogen gas and the buildup of computational errors from numerical integrations as one skilled in the art will understand. Accordingly, as the hydrogen generating reaction within the generator progresses toward completion, the hydrogen producing reaction front within the generator approaches the outlet of the generator, and as shown in FIG. 1. the $NH_3$ concentration increases in the resulting gas mixture. In particular, breakthrough of $NH_3$ occurs at the elapsed time corresponding to the point 20. Thus, at point 20 (corresponding to approximately 475 minutes of elapsed operating time of the hydrogen generator) there is a rapid increase in the $NH_3$ concentration. Thus, at approximately point 20 (or shortly thereafter) it is desirable that an embodiment of the present invention prevent further at least the ammonia in the gas flow from the hydrogen generator from reaching a device, such as a fuel cell.

In order to prevent the ammonia from entering a device, such as a fuel cell, prior to breakthrough, a small filter tube in the gas conduit between the hydrogen generator and the fuel cell may be packed with an ammonia getter having several grams of $NaHSO_4.H_2O$ (and optionally mixed with $CuCl_2.2H_2O$) followed by an amount of activated charcoal as a final filter. This combination of getter and filter is sufficient to prevent substantially all of the ammonia represented by the area under the curve of FIG. 1 prior to point 20 from reaching the device. However, once ammonia breakthrough occurs, both the getter and the filter rapidly become inoperative at filtering the ammonia from the gas stream, and the ammonia in the hydrogen stream is subsequently free to reach and contaminate the device unless otherwise prevented. Moreover, note that the amount of ammonia which the getter must filter prior to breakthrough may vary substantially depending on the operation of the hydrogen generator. The hydrogen is produced in the hydrogen generator by a reaction between ammonia and a reactant such as lithium aluminum tetrahydride ($LiAlH_4$). Such a reactant is heavier than $NH_3$, and accordingly it is preferable that as much useful hydrogen as possible be generated from the reactant provided in the generator. If a user causes the hydrogen generating reaction within the generator to proceed at a slow $H_2$ production rate (e.g., by controlling the amount of ammonia introduced into the reaction container of the generator), then the ammonia is consumed less efficiently and there may be relatively little ammonia left to enter the generated gas stream by the time the hydrogen generating reaction is no longer producing an effective amount of hydrogen. This due to the $H_2$ producing reaction being colder and less of the LiAlH4 may be thermally decomposed. However, if the user causes the hydrogen generating reaction within the generator to proceed at a rapid $H_2$ production rate, then the ammonia is consumed more efficiently and there may be substantially more ammonia left to enter the generated gas stream after the ammonia breakthrough time occurs. This is due to the reaction being hotter (+120 deg C.) and a proportionately larger fraction of $H_2$ being produced from thermal decomposition of LiAlH4. Accordingly, an excess of ammonia is preferred assuming that ammonia entering the gas stream can be prevented from entering a connected fuel cell (e.g., such prevention being performed by the present invention). Note that in at least some embodiments of the hydrogen generator, slow reactions routinely result in an $H_2/NH_3$ ratio of approximately 1.5 while hot/fast reactions can produce $H_2/NH_3$ a ratio of up to five.

In determining compounds or compositions that may be used as a breakthrough material for ammonia, the Applicants passed/flowed an $NH_3$ contaminated $H_2$ gas mixture through a glass tube packed with $CuCl_2.2H_2O$. The Applicants found that $CuCl_2.2H_2O$ reacted with the ammonia and formed a substantially gas impermeable solid or plug that was effective in blocking the flow of the gas mixture. In particular, when a 2% concentration of $NH_3$ in hydrogen was passed through a tube of hydrated $CuCl_2$ at approximately 300 mL/min, apparently a solid ammine complex is formed quickly where the gas mixture first contacts the $CuCl_2.2H_2O$. Subsequently, the solid expands, and then plugs the tube. During the experiment, the total flow rate at the outlet of the tube was measured with a simple flow meter, and the ammonia concentration was measured with an ion selective electrode. In the experiment, the resulting plug shut off the flow of the gas mixture in 8 minutes. Moreover, before the plug shut down the gas flow, a total of less than 5 mg of ammonia passed from the tube outlet. Due to such successful initial tests, embodiments of the present invention have been developed where effectively no ammonia escapes past the plug forming $CuCl_2.2H_2O$. Such embodiments and test results are described hereinbelow, and in particular, in relation to FIG. 9.

When hydrogen gas contaminated with $NH_3$ concentrations of about 100 ppm were used in tests similar to those described above, a plug did not form during 30 minutes of exposure. Additionally, it is believed that since the ligand bond energy for an ammine group is larger than that for water in a transition metal complex, ammonia in a $H_2$ gas should react with any number of hydrated complexes by exchanging water ligands for the ammine ligands. In particular, the following metal complexes are additionally believed to form plugs in the presence of ammonia at concentrations that correspond to an ammonia breakthrough:

(1) anhydrous $CuCl_2$,
(2) hydrated and anhydrous $CoCl_2$, and $AlCl_3$,
(3) hydrated cobalt (II and III) chloride and sulfate,
(4) hydrated copper (II) sulfate,
(5) hydrated chromium (II and III)) chloride and sulfate, and
(6) hydrated nickel (II) chloride and sulfate.

Accordingly, Applicants have tested anhydrous $CuCl_2$, hydrated and anhydrous $CoCl_2$, and anhydrous $AlCl_3$. Although these compounds may generate gas impermeable plugs, these compounds were found to be less effective than the hydrated $CuCl_2$ at similar $NH_3$ concentrations.

Figures 2, 3:
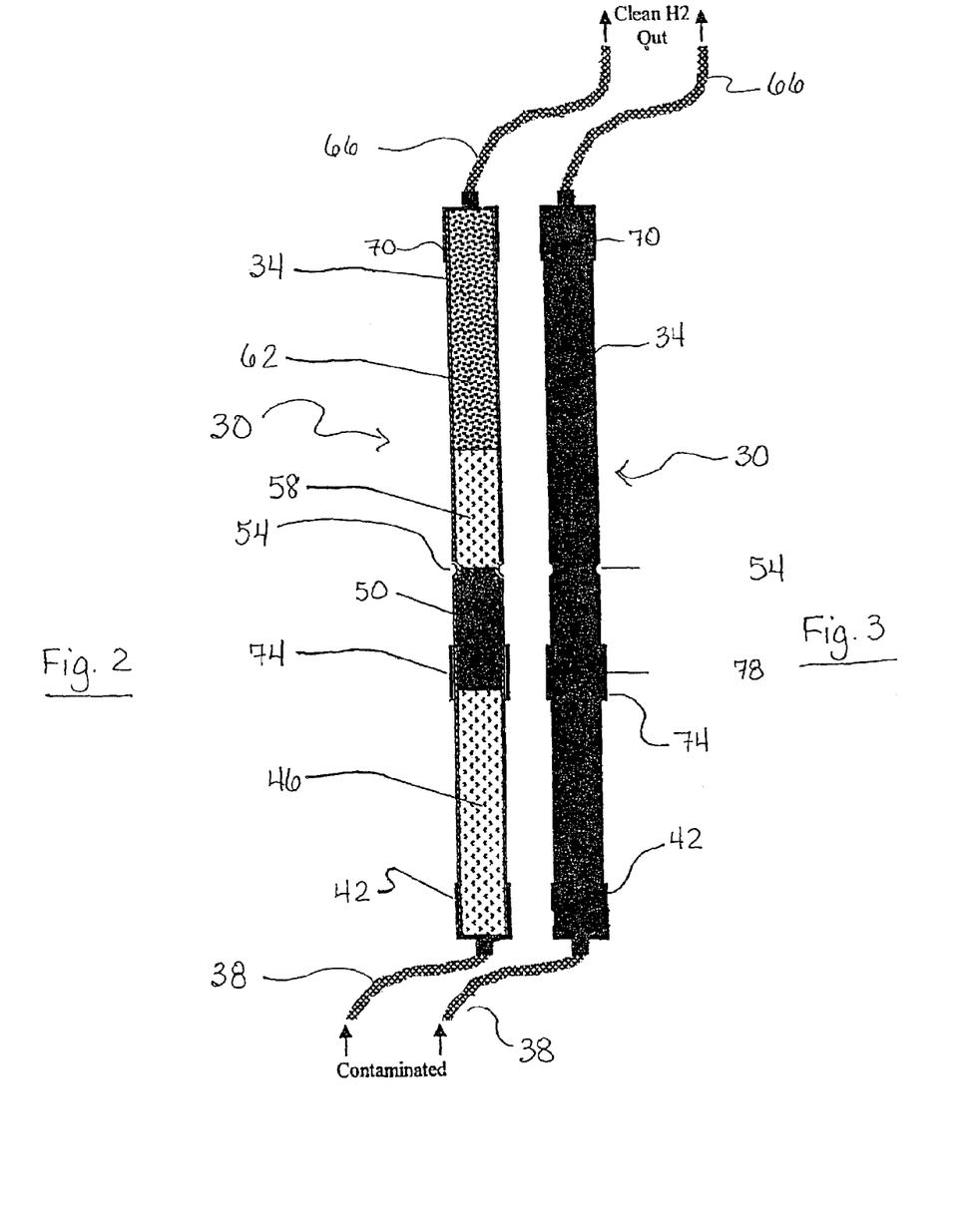
FIG. 2 shows a cross section an ammonia filter/fuse 30 according to the present invention, wherein hydrated $CuCl_2$ is used as the breakthrough detection material.
FIG. 3 shows an exterior view of the ammonia filter/fuse 30 of FIG. 2.
Figure 4A:
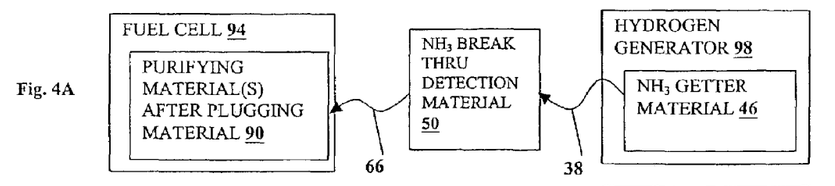
FIGS. 4A through 4F show alternative embodiments of the present invention, wherein the getter 46, the breakthrough detection material 50. and purifying materials 90 may be distributed such that one or more of these materials is incorporated into a device, such as a fuel cell 94, or the hydrogen generator 98.
Figure 4B:
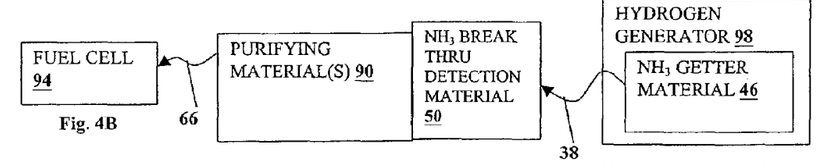
Figure 4C:
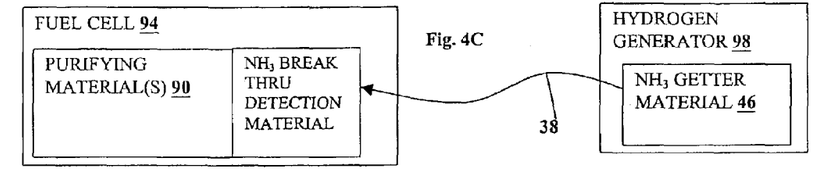
Figure 4D:
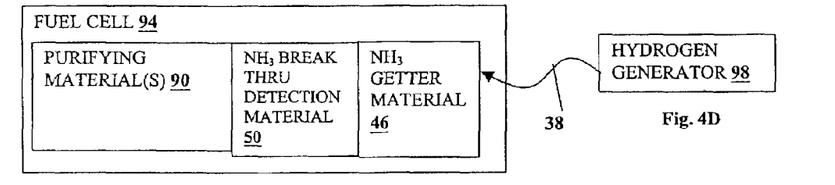
Figure 4E:
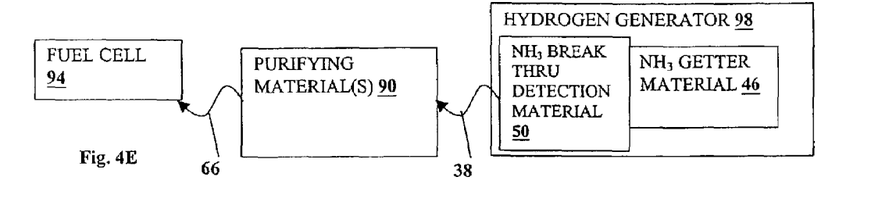
Figure 4F:
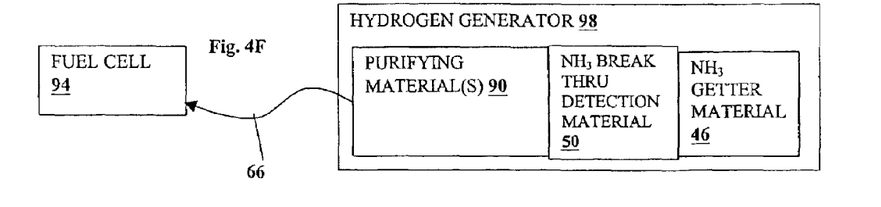

FIGS. 2 and 3 show two views of the same embodiment of an ammonia filter/fuse 30 according to the present invention, wherein hydrated $CuCl_2$ is used as the breakthrough detection material. The filter/fuse 30 is shown in cross section in FIG. 2, and FIG. 3 shows an external view. The filter/fuse 30, has an outer housing 34 which may be made of aluminum and may be substantially cylindrical. Gas from a hydrogen generator (not shown in FIGS. 2 and 3) is provided to the interior of the housing 34 by a gas conduit 38. The gas conduit 38 is operably sealed to an end cap 42 so that the gas stream in the conduit enters the interior of the housing 34. Note that the end cap 42 may also be made of aluminum, and may be sealed air-tightly to the housing 34 by an epoxy or other sealing method as one skilled in the art will understand. The first material the gas stream contacts within the housing 34 is an ammonia getter 46 (e.g., $NaHSO_4H_2O$ or other mixture of ammonia getter materials, each preferably mixed with $CuCl_2.2H_2O$). Down stream of the getter 46 and also within the housing 34 is an ammonia breakthrough detection material 50 such as, hydrated copper (II) chloride ($CuCl_2.2H_2O$). Note that the hydrated copper (II) chloride forms a substantially gas impermeable plug when exposed to an ammonia concentration of 2.0% or greater in the gas stream. Moreover, as mentioned above, hydrated copper (II) chloride also changes from light-green to dark blue when exposed to such an ammonia concentration. At the downstream end of the breakthrough detection material 50, the housing 34 has an annular recess 54 of reduced dimension in comparison to the remainder of the housing 34. Note that the annular recess may extend into the breakthrough detection material 50. During operation, at, e.g., a maximum ambient operating temperature of 50° C., a hydrogen generator may produce a hydrogen gas mixture at a pressure of 20 bars (300 psia). The recess 54 is designed to prevent the plug formed from a reaction between the hydrated copper (II) chloride and the ammonia from being displaced due to a gas pressure buildup on the upstream side of the plug. Note that in one embodiment where the housing 34 is substantially cylindrical, it is desirable that for a breakthrough detection material such as hydrated copper (II) chloride which forms a plug, the lengthwise extent of the hydrated copper (II) chloride in the direction of the gas flow is at least as great as the maximal diameter of the hydrated copper (II) chloride in the housing 34. More preferably, the lengthwise extent of the hydrated copper (II) chloride should be at least twice its maximal diameter. Additionally, in some embodiments, the length to diameter ratio may be in the range of 10 to 20. Note this extra length of the ammonia breakthrough detection material 50 may, in some alternative embodiments, be a replacement for a secondary $NH_3$ getter downstream from the material 50. Accordingly, the additional getter 58 (described immediately below) may not be needed in these alternative embodiments.

Downstream of the breakthrough material 50, is additional getter 58 followed by activated charcoal or carbon filter 62. The additional getter 58 removes any residual ammonia that bypasses the breakthrough detection material 50 prior to the full formation of a plug. The filter 62 captures any organic solvent vapor and any $CuCl_2.2H_2O$ vapor/impurities (e.g., chlorine). Accordingly, purified $H_2$ (with possibly traces of water included) exits the filter/fuse 30 and is conveyed via conduit 66 (sealed to end cap 70 which may be identical to end cap 42) to a device $H_2$ inlet (not shown).

FIGS. 2 and 3 additionally show an outer collar 74 which is tightly fitted to the housing 34 (e.g., by a sweat fit). The collar 74 includes a transparent window 78 therein. An opening into the interior of the housing 34 is provided underneath the collar 74 wherein the opening is aligned with the window 78 so that the breakthrough detection material 50 is visible through the window 78. Thus, for a breakthrough material 50 that changes color upon contact with a sufficient amount and/or concentration of ammonia, the color of the breakthrough material can be viewed by a user for determining whether ammonia breakthrough has occurred.

In operation, the getter 46 may be provided in a sufficient quantity so that under substantially all operating conditions, the ammonia in the $H_2$ gas stream prior to breakthrough is substantially fully absorbed by the getter 46. Additionally, any residual contaminants are absorbed by the carbon filter 62. However, once breakthrough occurs, ammonia (in sufficient quantities) contacts the breakthrough detection material 50 causing a plug to begin forming in the gas stream. Since some ammonia, as well as other contaminants, may escape past the forming plug, the getter 58 and the carbon filter 62 are provided in sufficient quantities to absorb virtually all remaining contaminants (except possibly water) prior to the purified gas stream entering the conduit 66. The $H_2$ flow restriction from the forming plug will cause the $H_2$ pressure at an inlet of an attached device to fall rapidly as the plug forms. If the device controller is programmed to notice this pressure drop, it can warn the operator that it is time replace the current hydrogen generator. Finally, once the plug is fully formed, the gas stream is prevented from reaching an attached device.

There can be numerous alternative embodiments of the present invention, wherein corresponding components to those described above are identically labeled. However, for simplicity, the corresponding components to the getter 58 and/or the carbon filter 62 have been identified as the purifying material(s) 90. FIGS. 4A through 4F show some of the alternative embodiments wherein the getter 46, the breakthrough detection material 50 and purifying materials 90 may be distributed such that one or more of these materials is incorporated into a device, such as, e.g., a fuel cell 94 as shown in the present figures, or the hydrogen generator 98. Thus, one or more of the getter 46, the breakthrough detection material 50, and purifying material(s) 90 reside within a housing for the fuel cell 94 or within the hydrogen generator 98, and accordingly may be subject to the conditions of the fuel cell or the hydrogen generator such as temperature. Moreover, at least the purifying material(s) 90 may be separately replaceable from that of the getter 46 and the breakthrough detection materials 50. Additionally, though not shown in FIGS. 4A through 4F, if the purifying material(s) 90 include, e.g., a comparable component to the getter 58 as well as a comparable component to the carbon filter 62, then these two components, in some embodiments, be separately provided such that, e.g., the carbon filter 62 is attached to the housing of the fuel cell 94 and the getter 58 is operably connected to the filter 62 via a conduit corresponding to conduit 66. One skilled in the art will readily appreciate other combinations that can be provided given the disclosures provided here.

Furthermore, in one embodiment, at least the breakthrough detection material 50, and purifying material(s) 90 may be provided in standardized sized and/or shaped containers so that a plurality of such standardized containers may be used in parallel depending on the $H_2$ and $NH_3$ flow characteristics from the hydrogen generator 98. Thus, hydrogen generators providing higher output $H_2$ flow rates and/or longer duration of $NH_3$ contaminated $H_2$ may provide the generated gas mixture to a plenum (not shown) which distributes the gas mixture to the plurality of containers.

Note that in another embodiment, there may be breakthrough detection material 50 containers that are separate from getter 46 containers, wherein one or more getter containers may be placed in series and/or in parallel upstream of, e.g., a single detection material container. Thus, depending on the $H_2$ and $NH_3$ flow characteristics of the hydrogen generator 98, a sufficient number of getter containers are placed upstream of the breakthrough detection material container so that the getter material does not become saturated with $NH_3$ until the ammonia breaks though into the generated gas mixture.

In another embodiment, all getter material may be placed solely downstream of the breakthrough detection material 50. Note that this is possible in that for at least some breakthrough detection materials 50 and hydrogen generators 98, the concentration of ammonia contaminating the hydrogen prior to breakthrough is insufficient to cause a change in the breakthrough detection material that is sufficient to cause a premature termination of the gas mixture flow. Accordingly, one or more getter material containers may be placed downstream of a breakthrough detection container to absorb ammonia until there is a sufficient change in the breakthrough material to terminate the $H_2$ and $NH_3$ mixture from the hydrogen generator 98.

Figures 5, 6:
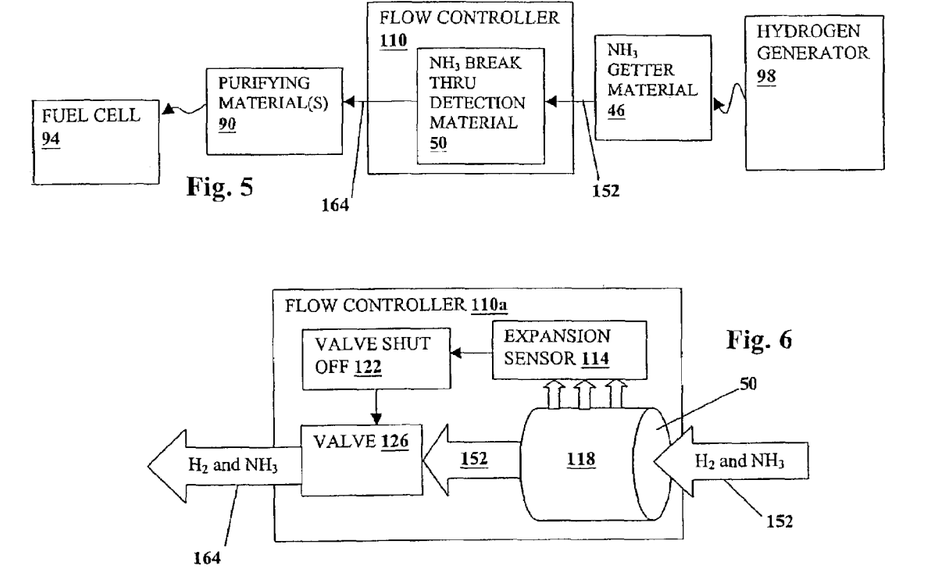
FIG. 5 shows another embodiment of the present invention wherein the generated gas mixture flows through a flow controller 110 for controlling (and in particular, preventing the flow of generated gas from reaching a fuel cell) when there is an excessive concentration of ammonia.
FIG. 6 shows one embodiment of the flow controller 110 (labeled herein as 110a), wherein an expansion sensor 114 detects a change in volume of the breakthrough detection material 50 as it reacts with the $NH_3$.

FIG. 5 shows another embodiment of the present invention wherein the generated gas mixture flows through a flow controller 110 for controlling (and in particular, preventing the flow of generated gas from reaching a device) when there is an excessive concentration of ammonia. The flow controller 110 having, e.g., the breakthrough detection material 50 included, terminates or prevents the flow of the generated gas mixture from the hydrogen generator 98 when the $NH_3$ concentration in the gas flow is approximately in the range of approximately 2.0% or greater. Note that the flow controller 110 may have various embodiments. For example, FIG. 6 shows one embodiment of the flow controller 110 (labeled herein as 110a) wherein an expansion sensor 114 detects a change in volume of the breakthrough detection material 50 as it reacts with the $NH_3$. Note that the breakthrough detection material 50 may be shaped so that the generated gas mixture reacts with the breakthrough detection material in a manner that causes this material to expand in a predetermined direction (e.g., increasing the diameter of the cylinder 118 of breakthrough detection material. Note that the expansion sensor 114 may be substantially mechanical and having a lever (not shown) for releasing a spring loaded shutoff device such as valve shut off 122 for terminating the gas mixture flow by activating a valve 126.

Figure 7:
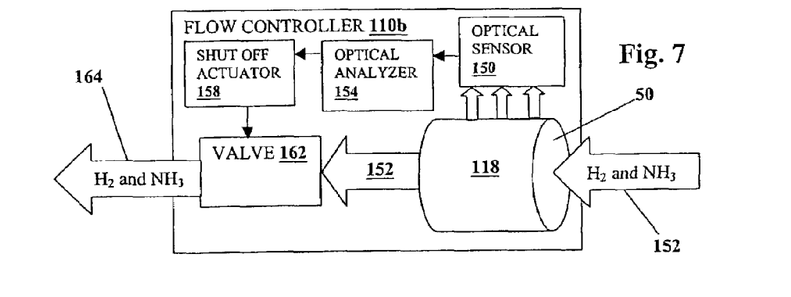
FIG. 7 shows an alternative embodiment of the flow controller 110 (this controller being labeled 110b), wherein optical and electronic components may be used therein.

An alternative embodiment of the flow controller 110 is shown in FIG. 7 (this controller being labeled 110b), wherein optical and electronic components may be used therein. In particular, an optical sensor 150 may be provided for optically sensing a predetermined change in the breakthrough detection material 50 such as a change in size, opacity, density, and/or color of the breakthrough detection material when the gas flow 152 includes a concentration of ammonia indicative of a breakthrough. For example, if the breakthrough detection material 50 is $CuCl_2.2H_2O$, this material changes color from light-green to dark blue upon reacting with a gas mixture having approximately a 2.0% or greater ammonia concentration. Thus, the optical sensor 150 may include a reflective photosensor using a red LED to optically interrogate the $CuCl_2.2H_2O$. Since the blue ammine complexes, resulting from a reaction with $NH_3$, absorbs red/orange light at about 600-nm, a gradual decrease in reflected LED energy would indicate the onset of ammonia breakthrough. Accordingly, signals from the optical sensor 150 are provided to an optical analyzer 154 for determining when a predetermined color, color change, and/or rate of change is detected. In turn, when the optical analyzer 154 detects a predetermined ammonia related change in the breakthrough detection material 50, a command is output to the shut off actuator 158 (or fuel cell 94) instructing this actuator (or fuel cell 94) to close the valve 162 and thereby terminate the output gas flow 152 (which may include trace amounts of $NH_3$).

Note that in one embodiment of FIG. 7, only a small amount of $CuCl_2.2H_2O$ may be provided in the gas mixture flow stream 152. For example, a $CuCl_2.2H_2O$ coated surface may be inserted into the gas mixture flow, e.g., within the cylinder 118 which in this embodiment may be glass or some other optically transparent material having a receptacle (not shown) for holding, for instance, a $CuCl_2.2H_2O$ coated substrate. Thus, light from a red light emitting diode can be directed to such a coated surface and the optical characteristics of light reflected therefrom can be analyzed by a optical analyzer 154. Note, that in this embodiment of the flow controller 110b, the flow controller may be reusable in that if the $CuCl_22H_2O$ coated surface is replaceable (e.g., like film in a camera) then the coated surface may be the only component requiring replacement between high ammonia concentration detections. Moreover, the shut off actuator 158 may automatically open the valve 162 when a new $CuCl_2.2H_2O$ coated surface is inserted into the flow controller 110b.

In another embodiment, the filter/fuse 30 of FIGS. 2 and 3 may be additionally equipped with a gas pressure differential device that is activated by the difference in pressure that results on the opposite sides of the resulting plug. Accordingly, activation of the pressure differential device may cause a valve to shut thereby permanently preventing any the gas flow from leaking from the plug. Note that this embodiment may be useful in conditions were a user may not be available (or may be incapacitated) and the device (e.g., fuel cell) may be left unattended for long periods of time.

Figure 8:
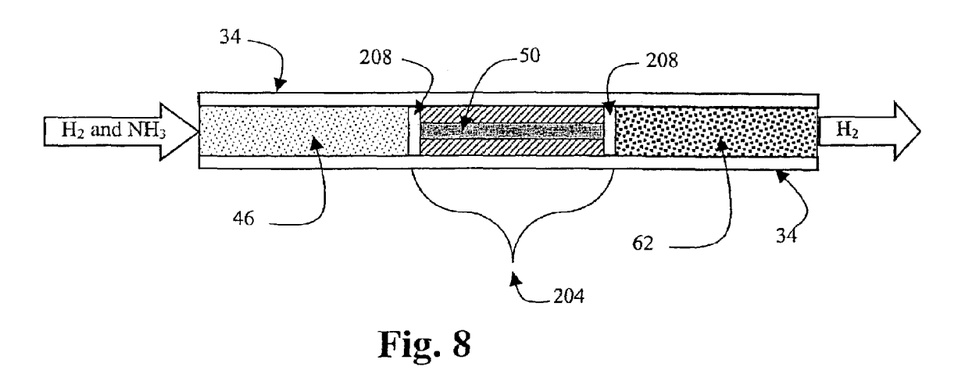
FIG. 8 shows an alternative embodiment of the ammonia filter/fuse 30.

A further embodiment of the filter/fuse 30 of the present invention is shown in FIG. 8. Contained within the outer housing 34, is a restricted diameter portion 204 (e.g., having a diameter of approximately 3 mm and a length of approximately 46 mm) having therein the breakthrough detection material 50 (e.g., $CuCl_22H_2O$). At each end of the restricted diameter portion 204 is a stainless steel frit (or breakthrough detection material retainer that is gas permeable) 208 for retaining the breakthrough detection material 50 therein. Downstream of the portion 204 is a carbon or charcoal filter 62 substantially identical the one of FIG. 2. Upstream of the portion 204 is a getter 46, which may include a mixture of $CuCl_22H_2O$ and $NaHSO_4H_2O$. Note that $CuCl_22H_2O$ is an effective getter in that it can absorb approximately 1/10 of its weight of ammonia. However, to assure that an accumulation of captured ammonia in a getter having $CuCl_22H_2O$ does not prematurely form a plug (or other indication of ammonia breakthrough), the $CuCl_22H_2O$ in the getter 46 is mixed with preferably a porous compressible material that can compress with an expansion caused by the reaction between $CuCl_22H_2O$ and ammonia. There are numerous such porous compressible materials that may be mixed into the getter 46 such as vermiculites. However, it is also preferable that the porous compressible material also absorb ammonia without adversely effecting the functioning of the filter/fuse 30. In one embodiment, since $NaHSO_4H_2O$ is porous and compressible, it may be mixed with $CuCl_22H_2O$ in a range of approximately equal parts to a mixture of approximately 20 parts $NaHSO_4H_2O$ to 80 parts of $CuCl_22H_2O$ for thereby obtaining the getter 46.

Figure 9:
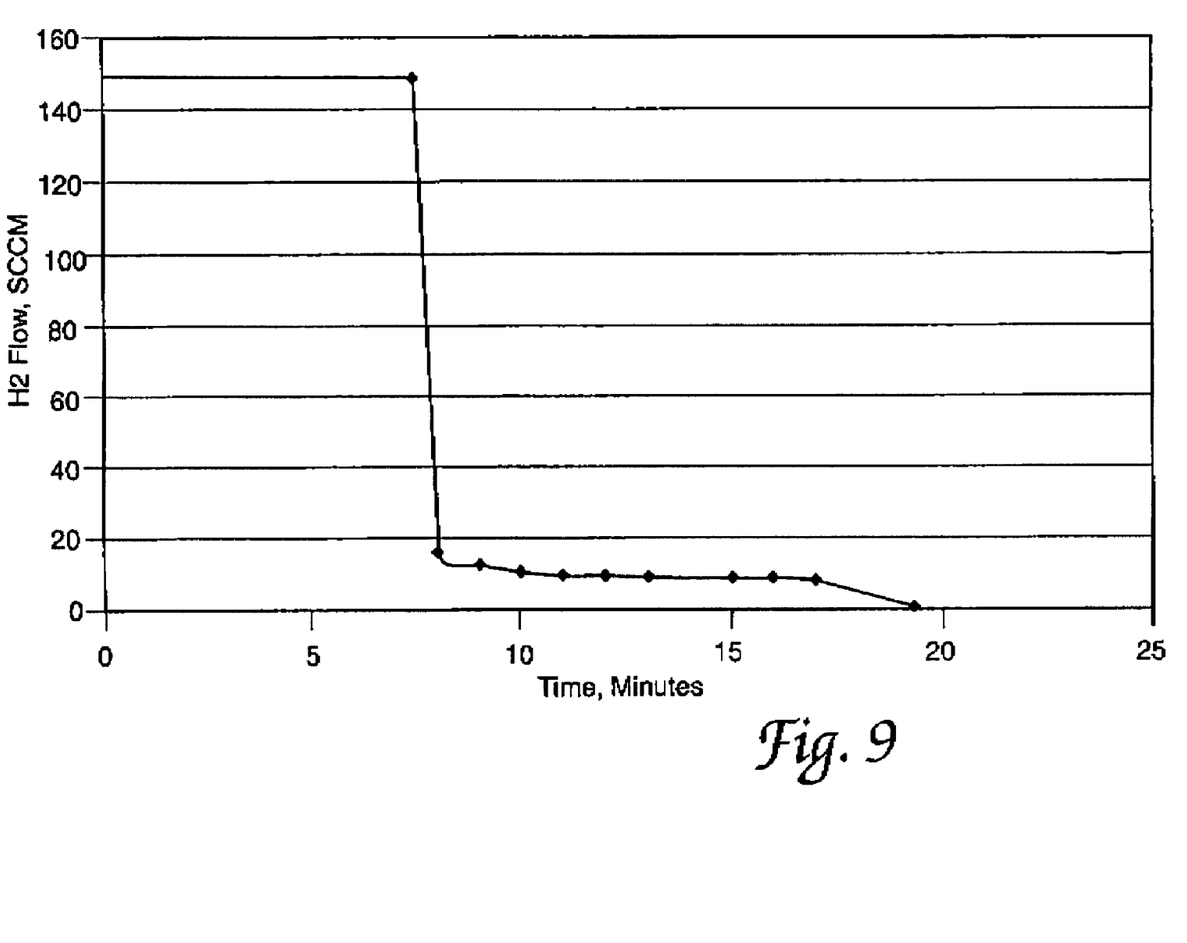
FIG. 9 shows a graph of the effectiveness of $CuCl_2$ $2H_2O$ in stopping a hydrogen/ammonia gas flow.

FIGS. 9 and 10 illustrate the effectiveness of $CuCl_2 2H_2O$ in forming a gas impervious barrier when it reacts with a sufficient amount of ammonia. In particular, these figures show graphs of the effectiveness of $CuCl_2 2H_2O$ in an embodiment of filter/fuse 30 of FIG. 8, wherein:

(a) the breakthrough detection material 50 is 0.5 grams of $CuCl_2 2H_2O$;

(b) the getter 46 is 6.1 grams of a mixture of 25% (by weight) of $NaHSO_4 H_2O$ and 75% by weight $CuCl_2 2H_2O$; and (c) the filter 62 is 1.8 grams of activated carbon.

A constant gas mixture of 90% hydrogen and 10% ammonia was input to this embodiment of the filter/fuse 30. The gas mixture was provided at 21° C., 100 psi, and an initial gas flow rate of 165 cc/min (sccm) at the getter 46 inlet. FIG. 9 shows a graph of the difference in pressure between the gas inlet and the gas outlet of the present embodiment of the fuse/filter 30 over time. Note that the difference in inlet and outlet gas pressures remains relatively small until the gas mixture is provided to the filter/fuse 30 for an elapsed time corresponding to $T_1$ (i.e., about 103 minutes). From $T_1$ to $T_2$ (i.e., about 107 minutes) a plug in the breakthrough detection material 50 commences to restrict the gas flow through the filter/fuse 30 sufficiently to dramatically increase the pressure differential. Finally, from $T_2$ to $T_3$ the plug seals off the gas flow substantially completely. FIG. 10 shows a corresponding graph of the hydrogen gas flow out of the filter/fuse 30 from time $T_2$ to time $T_3$. Note that at time $T_3$ there is virtually no gas flow through the filter/fuse 30.

Although the present invention has been substantially described in the context of gas flow involving hydrogen, ammonia and a device that utilizes hydrogen, other gases and devices can be applicable. Chemical trapping (and subsequent blocking of flow) of trace contaminant gas species other than ammonia in a process feed gas could be provided, such as by using transition metal complexes. Gases other than ammonia that can be chemically sequestered through heterogeneous phase reactions with solid phase transition metal complexes can include, but are not limited to: $CO$, $NO_x$, $SO_x$, $HF$, $HCl$, $HCN$, $H_2S$, $PH_3$, $Cl_2$, $O_2$, $CO_2$, $C_2H_2$, $C_2H_4$, and $H_2O$ (carbon monoxide, nitrogen oxides, sulfur dioxide and trioxide, hydrogen fluoride, hydrogen chloride, hydrogen cyanide, hydrogen sulfide, phosphine, chlorine, oxygen, carbon dioxide, acetylene, ethylene, and water).

Typical reactions that are known between available transition metal complexes and such trace contaminant gases include, but are not limited to, Ligand Substitution Reactions, Insertion Reactions, and Oxidative Addition Reactions. The selection of a particular transition metal complex for a given trace gas to be sequestered, is dependent on the physical characteristics of the complex. A sufficient density change is required between the reactants and complex to be useful in modulating or terminating the gas flow once a sufficient amount of trace gas has been absorbed or sequestered by the complex. Also the selected transition metal complex should not be reactive to the primary carrier or feed gas that is being purified or filtered of the trace gas.

The foregoing discussion of the invention has been presented for purposes of illustration and description. Further, the description is not intended to limit the invention to the forms disclosed herein. Consequently, variation and modification commensurate with the above teachings, within the skill and knowledge of the relevant art, are within the scope of the present invention. The embodiments described hereinabove are further intended to explain the best modes presently known of practicing the invention and to enable others skilled in the art to utilize the invention as such, or in other embodiments, and with the various modifications required by their particular application or uses of the invention.

What is claimed is:

1. A method for controlling the flow of hydrogen and ammonia from a hydrogen generator during a breakthrough, the method comprising:

providing a housing forming a chamber, the housing having an inlet and outlet;

packing the chamber of the housing with hydrated copper (II) chloride;

moving the flow of hydrogen and ammonia into the hydrated copper (II) chloride packed in the chamber of the housing;

wherein the hydrated copper (II) chloride is packed within the chamber of the housing with sufficient density to allow the flow of hydrogen and ammonia to pass through the hydrated copper (II) chloride when ammonia is below a breakthrough concentration and to allow the formation of the gas impermeable plug when at least the breakthrough concentration of ammonia within the flow reacts with the hydrated copper (II) chloride, thus preventing the flow of hydrogen and ammonia from exiting the outlet of the housing by blocking the flow with the gas impermeable plug.

2. The method of claim 1 wherein the breakthrough concentration of ammonia is 2 percent or greater by volume of the flow.

3. A method for controlling the flow of hydrogen and ammonia from a hydrogen generator during a breakthrough, the method comprising:

providing a housing forming a chamber, the housing having an inlet and outlet;

packing the chamber of the housing with hydrated copper (II) chloride;

moving the flow of hydrogen and ammonia into the hydrated copper (II) chloride packed in the chamber of the housing;

wherein the hydrated copper (II) chloride is packed within the chamber of the housing with sufficient density to allow the flow of hydrogen and ammonia to pass through the hydrated copper (II) chloride when ammonia is below a breakthrough concentration and to allow the formation of the gas impermeable plug when at least the breakthrough concentration of ammonia within the flow reacts with the hydrated copper (II) chloride, thus preventing the flow of hydrogen and ammonia from exiting the outlet of the housing by blocking the flow with the gas impermeable plug.

4. The method of claim 3 wherein the breakthrough concentration of ammonia is 2 percent or greater by volume of the flow.

* * * * *